(12) United States Patent
Kato et al.

(10) Patent No.: US 9,649,028 B2
(45) Date of Patent: May 16, 2017

(54) OPHTHALMOLOGICAL DEVICE

(71) Applicant: Tomey Corporation, Nagoya-shi (JP)

(72) Inventors: Chihiro Kato, Nagoya (JP); Yuji Nozawa, Nagoya (JP); Keiichiro Okamoto, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 0 days.

(21) Appl. No.: 15/008,637

(22) Filed: Jan. 28, 2016

(65) Prior Publication Data
US 2016/0220109 A1 Aug. 4, 2016

(30) Foreign Application Priority Data
Jan. 29, 2015 (JP) .................. 2015-015950

(51) Int. Cl.
*A61B 3/10* (2006.01)
*A61B 3/107* (2006.01)
*A61B 3/00* (2006.01)
*A61B 3/14* (2006.01)

(52) U.S. Cl.
CPC ............ *A61B 3/107* (2013.01); *A61B 3/0025* (2013.01); *A61B 3/102* (2013.01); *A61B 3/1005* (2013.01); *A61B 3/14* (2013.01)

(58) Field of Classification Search
USPC ....................................................... 351/212
See application file for complete search history.

(56) References Cited

U.S. PATENT DOCUMENTS
2012/0140174 A1  6/2012  Hee et al.

FOREIGN PATENT DOCUMENTS
| JP | 2008-167777 A | 7/2008 |
| JP | 2008-188047 A | 8/2008 |
| JP | 2012-096098 A | 5/2012 |

*Primary Examiner* — Jack Dinh
(74) *Attorney, Agent, or Firm* — Shumaker, Loop & Kendrick, LLP

(57) ABSTRACT

An ophthalmological device calculates a cornea surface shape of an eye to be examined. The ophthalmological device includes a ring image photographic optical system configured to radiate a plurality of concentric ring light to the cornea surface of the eye and take reflected images of the plurality of ring light reflected from the cornea surface of the eye, an interference optical system configured to radiate measurement light to the eye and detect interfering light composed of reflected light of the measurement light reflected from the eye and predetermined reference light. The shape of the cornea anterior surface of the eye is calculated form the reflected images of the plurality of ring light, the thicknesses of the cornea of the eye at the plurality of incident positions is calculated from the interfering light, and the posterior surface shape of the cornea of the eye is calculated based on these two results.

6 Claims, 4 Drawing Sheets

OPHTHALMOLOGICAL DEVICE

CROSS-REFERENCE TO RELATED APPLICATION

This application claims priority to Japanese Patent Application No. 2015-015950 filed on Jan. 29, 2015, the entire contents of which are hereby incorporated by reference into the present application.

TECHNICAL FIELD

The present application is related to an ophthalmological device to examine an eye.

BACKGROUND

A treatment of implanting an intraocular lens (IOL) in a patient's eye may be conducted. For example, in a cataract surgery, after a crystalline lens is removed from inside the patient's eye, an intraocular lens (IOL) is inserted into the patient's eye. For determining the power of the intraocular lens, eye characteristics data such as the eye axial length and the cornea curvature (cornea refractivity) of the targeted eye are measured in advance, and based on the obtained eye characteristics data, the power of the intraocular lens is determined in accordance with a known IOL calculation formula. Particularly, in order to properly prescribe an intraocular lens for an eye with a cornea disease or an eye having undergone a refraction correcting surgery, it is necessary to calculate the refractivity of the entire cornea by measuring the curvature radiuses of the anterior and posterior surfaces of the cornea of an eye to be examined, and the like. Japanese Patent Application Publication No. 2008-167777 discloses an ophthalmological device for examining the thickness of the cornea of an eye to be examined. The ophthalmological device in Japanese Patent Application Publication No. 2008-167777 includes an interference optical system, which radiates measurement light to an eye to be examined and detects interfering light composed of reflected light reflected from the eye to be examined and reference light which interfere with each other. The ophthalmological device detects the interfering light at a plurality of measurement points of the eye to be examined. Then, the position of the cornea's anterior surface and the position of the cornea's posterior surface at each measurement point are specified based on the interfering light detected at the plurality of measurement points. Thus, the thickness of the cornea at each measurement point of the eye to be examined is obtained.

BRIEF SUMMARY

As described above, in order to properly prescribe an intraocular lens, the shape (radius of curvature) of the cornea anterior surface and the shape (radius of curvature) of the cornea posterior surface of a targeted patient are needed to be obtained. In conventional technology, the shape of the cornea anterior surface is measured, and the shape of the cornea posterior surface is estimated from the shape of the cornea anterior surface using an empirical formula. Therefore, error in the estimated shape of the cornea posterior surface hinders proper prescription of the intraocular lens. Therefore, it is desired to provide an ophthalmological device capable of measuring the shape of the cornea posterior surface.

The present application has been made in view of the above circumstances, and an object thereof is to provide an ophthalmological device capable of measuring the shape of the cornea posterior surface.

An ophthalmological device disclosed in this application comprises a ring image photographic optical system, an interference optical system and a processor. The ring image photographic optical system is configured to radiate a plurality of concentric ring light around a cornea apex to a cornea surface of an eye to be examined and take reflected images of the plurality of ring light reflected from the cornea surface of the eye. The interference optical system is configured to radiate measurement light to the eye, and detect interfering light composed of reflected light of the measurement light reflected from the eye and predetermined reference light. The interference optical system is further configured to change an incident position of the measurement light radiated to the eye. The processor is configured to calculate (1) the anterior surface shape of the cornea of the eye based on the reflected images of the plurality of ring light obtained in the ring image photographic optical system, (2) the thickness of the cornea at the incident positions based on the interfering light at the incident positions obtained in the interference optical system, and (3) the posterior surface shape of the cornea of the eye based on the anterior surface shape of the cornea of the eye and thicknesses of the cornea at the plurality of incident positions.

In the ophthalmological device, the shape of the cornea anterior surface of the eye to be examined is calculated based on the reflected images of the plurality of ring light obtained in the ring image photographic optical system. In addition, the thicknesses of the cornea at the plurality of incident positions are calculated based on the interfering light at the plurality of incident positions obtained in the interference optical system. Each position of the cornea posterior surface can be specified from the corresponding position of the cornea anterior surface and the thickness of the cornea at this position. Therefore, the processor calculates the shape of the cornea posterior surface using the position of the cornea posterior surface specified from the calculated shape of the cornea anterior surface and the calculated thicknesses of the cornea of the eye to be examined. The ophthalmological device enables measurement of the shape of the cornea posterior surface.

DETAILED DESCRIPTION

In the ophthalmological device disclosed in the present application, each of the preset incident positions may be on a circumference of a preset circle which is preset so as to encircle a cornea apex of the eye, and the interference optical system may be configured to radiate the measurement light at each of the preset incident positions. The processor may be configured to determine the thicknesses of the cornea of the eye at the preset incident positions on the circumference of the preset circle. Such a configuration enables each position of the ring light radiated by the ring image photographic optical system and each position of the measurement light radiated by the interference optical system to correspond to each other, thereby enabling accurate calculation of the shape of the cornea posterior surface.

In the ophthalmological device disclosed in the present application, the interference optical system may further comprise an optical member configured to radiate the measurement light such that the measurement light enters the eye parallel to an optical axis of the eye while the incident position of the measurement light is changed by the interference optical system. Such a configuration increases the light intensity of the reflected light (reflected light of the measurement light) from the eye to be examined, thereby enabling accurate calculation of the thickness of the cornea.

The ophthalmological device disclosed in the present application may further comprise an incident position sensor configured to detect the incident position of the measurement light that is changed by the interference optical system. In such a configuration, each position at which the measurement light has been actually radiated is detected, thereby enabling accurate calculation of the shape of the cornea posterior surface.

Embodiment 1

Figure 1:
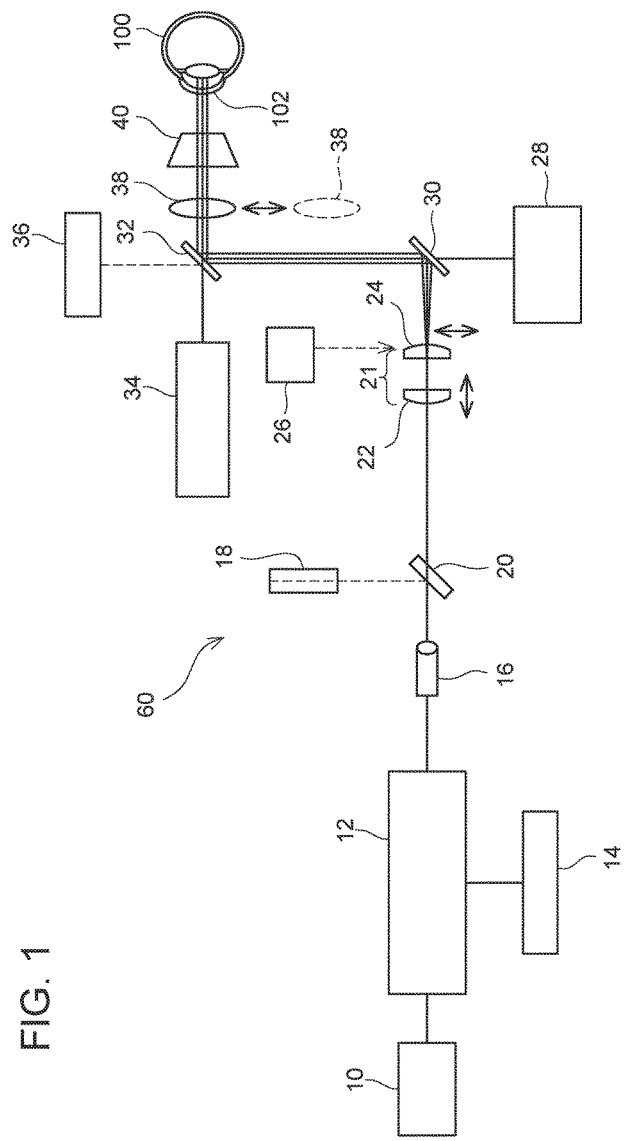
FIG. 1 is a schematic configuration diagram of an optical system of an ophthalmological device according to the present embodiment.

As shown in FIG. 1, the ophthalmological device of the present embodiment includes a measurement unit 60 for examining a cornea 102 of an eye to be examined 100. The measurement unit 60 includes: a ring image photographic optical system (28, 30, 32, 40) for measuring the shape of the anterior surface of the cornea 102; an interference optical system (10, 12, 14, 16, 18, 20, 22, 24, 30, 32, 36, 38) for measuring the thickness of the cornea 102; and an alignment mechanism 34 for aligning the measurement unit 60 in a predetermined positional relationship with respect to the eye to be examined 100.

The ring image photographic optical system (28, 30, 32, 40) radiates a plurality of concentric ring light to the anterior surface (front surface) of the cornea 102, and takes reflected images of the plurality of ring light reflected from the anterior surface of the cornea 102. The ring image photographic optical system includes a cone 40, a lighting device 42 (not shown in FIG. 1, but shown in FIG. 2) using an LED, and an imaging device 28 for taking reflected images of the ring light reflected from the anterior surface of the cornea 102.

The cone 40 is an object which is hollow and has a circular truncated cone shape, and is made of transparent resin. A transparent film on which a concentric pattern is printed is applied on the inner wall surface of the cone 40. The outer wall surface of the cone has a coat to reflect light.

Figure 4:
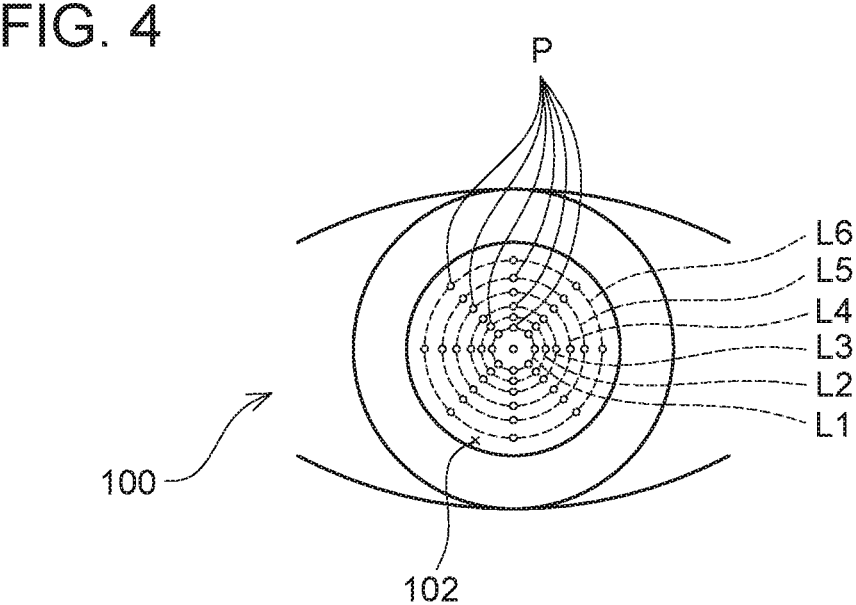
FIG. 4 is a diagram showing both of ring-like light radiated to an eye to be examined and incident positions of measurement light radiated to the eye to be examined.

The lighting device 42 is placed at the back side (a side opposite to the eye to be examined 100) of the cone 40. Light radiated from the lighting device 42 is scattered in the cone 40 and partially blocked by the transparent film Thus, concentric ring light are projected (radiated) to the cornea 102 of the eye to be examined 100. That is, as shown in FIG. 4, six ring light L1 to L6 are projected on the front surface of the cornea 102 of the eye to be examined 100. As described later, in projection of the ring light L1 to L6 on the eye to be examined 100, the measurement unit 60 is positioned with respect to the apex of the cornea 102 of the eye to be examined 100. Therefore, the ring light L1 to L6 projected on the eye to be examined 100 are positioned concentrically with respect to the apex of the cornea 102.

The imaging device 28 takes an anterior eye image of the eye to be examined 100 and reflected images of the ring light L1 to L6 reflected from the anterior surface of the cornea 102. That is, the anterior eye image of the eye to be examined 100 and the reflected images of the ring light L1 to L6 are guided to the imaging device 28 via mirrors 32 and 30. The anterior eye image of the eye to be examined 100 and the reflected images of the ring light L1 to L6, taken by the imaging device 28, are inputted to a processor 50 described later. In addition, the anterior eye image of the eye to be examined 100 and the reflected images of the ring light L1 to L6 are displayed on a monitor 44.

The interference optical system (10, 12, 14, 16, 18, 20, 22, 24, 30, 32, 36, 38) radiates measurement light to the eye to be examined 100, and detects interfering light composed of a combination of reflected light (reflected light based on the measurement light) reflected from the eye to be examined 100 and reference light. The interference optical system includes: a light source 10; a measurement optical system which radiates light from the light source 10 to the inside of the eye to be examined 100 and guides reflected light thereof; a reference optical system which radiates light from the light source 10 to a reference plane and guides reflected light thereof; and a light receiving element 14 which receives interfering light composed of a combination of the reflected light guided by the measurement optical system and the reference light guided by the reference optical system.

The light source 10 is a wavelength-sweeping-type (wavelength-scanning-type) light source, and the wavelength of light emitted therefrom varies in a predetermined cycle. In the present embodiment, while the wavelength of light emitted from the light source 10 is varied, reflected light from the eye to be examined 100 and the reference light are caused to interfere with each other, and the resultant interfering light is measured. As described later, the measured interfering light (interfering signal) is subjected to Fourier transform, whereby the position of the anterior surface and the position of the posterior surface of the cornea 102 of the eye to be examined 100 are specified.

The measurement optical system includes a collimator lens 16, a beam splitter 20, a beam expander 21, the mirrors 30 and 32, a lens 38, and a light detector 36. A part of light emitted from the light source 10 is radiated to the eye to be examined 100 via the collimator lens 16, the beam splitter 20, the beam expander 21, the mirrors 30 and 32, and the lens 38. Reflected light from the eye to be examined 100 is guided to an interferometer 12 and the light receiving element 14 via the lens 38, the mirrors 32 and 30, the beam expander 21, the mirror 34, the beam splitter 20, and the collimator lens 16. The functions of the beam expander 21, the light detector 36, and the lens 38 will be later described in detail.

The reference optical system includes a reference mirror (not shown) placed in the interferometer 12. That is, light emitted from the light source 10 is partially branched to be radiated to the reference mirror placed in the interferometer 12. The light radiated to the reference mirror is reflected by the reference mirror, whereby reference light is generated.

The interferometer 12 combines the light (reference light) guided by the reference optical system and the light (measurement light) guided by the measurement optical system, to obtain interfering light. The light receiving element 14 detects the interfering light obtained by the interferometer 12. As the light receiving element 14, for example, a photodiode can be used.

Between the collimator lens 16 and the beam expander 21, the beam splitter 20 and a glass 18 are placed. A part of light emitted from the light source 10 passes through the collimator lens 16, is reflected by the beam splitter 20, and then is radiated to the glass 18. The light radiated to the glass 18 is reflected by an end surface of the glass 18. The light reflected by the end surface of the glass 18 is guided to the interferometer 12 and the light receiving element 14 via the beam splitter 20 and the collimator lens 16. The position of the glass 18 is fixed, and therefore the optical path length of the light reflected by the end surface of the glass 18 does not change but remains constant. In the present embodiment, a result of measurement of the eye to be examined 100 is corrected using the interfering light obtained by combining the light reflected by the end surface of the glass 18 and the reference light.

Here, the functions of the beam expander 21, the light detector 36, and the lens 38 provided in the measurement optical system will be described. The beam expander 21 includes: a convex lens 22 placed on the light source 10 side; a convex lens 24 placed on the eye to be examined 100 side; and a drive mechanism 26 which moves forward and backward the convex lens 22 relative to the convex lens 24 in the optical-axis direction (z-axis direction), and moves the convex lens 24 in a plane (xy plane) orthogonal to the optical axis. The convex lens 22 and the convex lens 24 are placed on the optical axis, and change the position of the focal point of the entering parallel light. That is, the drive mechanism 26 drives the convex lens 22 in the optical-axis direction, whereby the position of the focal point of light radiated to the eye to be examined 100 is changed in the depth direction of the eye to be examined 100. Specifically, from the state in which the interval between the convex lens 22 and the convex lens 24 is adjusted so that light radiated from the convex lens 24 becomes parallel light, if the convex lens 22 is moved away from the convex lens 24, light radiated from the convex lens 24 becomes convergent light, and if the convex lens 22 is moved to approach the convex lens 24, light radiated from the convex lens 24 becomes divergent light. Thus, by causing the position of the focal point of light radiated to the eye to be examined 100 to match the anterior surface of the cornea 102 of the eye to be examined 100, the intensity of light reflected from the surface can be increased, and the position of the surface can be accurately detected.

The convex lens 24 is two-dimensionally movable in a plane (xy plane) orthogonal to the optical axis. That is, the drive mechanism 26 two-dimensionally drives the convex lens 24 relative to the convex lens 22 in a plane (xy plane) orthogonal to the optical axis. Thus, the position (incident position) on the eye to be examined 100 at which light from the light source 10 is incident is two-dimensionally changed on the eye to be examined 100. Specifically, in FIG. 4 showing a front view of the eye to be examined 100, the incident position of the light is two-dimensionally changed in the plane (xy plane). More specifically, if the convex lens 24 is moved relative to the convex lens 22 in the y direction, the incident position is also changed in the y direction. If the convex lens 24 is moved relative to the convex lens 22 in the x direction, the incident position is also changed in the x direction. Thus, by moving the convex lens 24 relative to the convex lens 22 in the x direction and/or the y direction, the incident position is changed in the xy plane. In the present embodiment, the measurement light is scanned so as to be radiated to the same positions (concentric positions centered on the apex of the cornea 102) as the ring light L1 to L6 radiated to the eye to be examined 100, and the thicknesses of the cornea 102 at a plurality of incident positions P (measurement points) on a trajectory on which the measurement light is scanned are measured.

The incident position of the measurement light radiated from the interference optical system to the eye to be examined 100 is detected by the position detector 36. That is, when the drive mechanism 26 moves the convex lens 24 in the xy plane, the incident position of the measurement light radiated to the eye to be examined 100 is thereby changed, and the incident position of the measurement light incident on the mirror 32 is also changed. The light incident on the mirror 32 is partially reflected by the mirror 32 to be radiated to the eye to be examined 100, and partially transmits through the mirror 32 to be detected by the position detector 36. The position detector 36 detects the position on the mirror 32 at which the light is incident. Thus, it becomes possible to accurately specify the incident position of the measurement light radiated to the eye to be examined 100.

Figure 6:
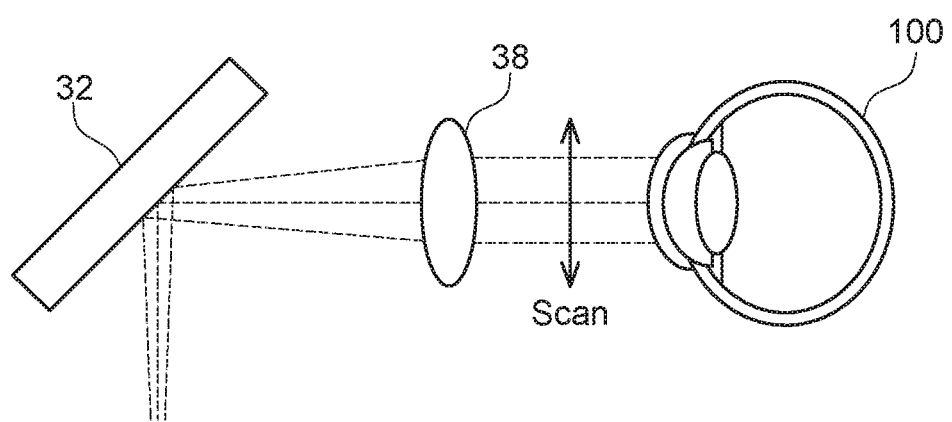
FIG. 6 is a diagram for explaining a function of a lens 38.

If the incident position of the measurement light radiated to the eye to be examined 100 is shifted from the position of the apex of the cornea 102, the intensity of light reflected from the eye to be examined 100 might reduce. As a result, the intensity of the interfering light detected by the light detector 14 might reduce. In the present embodiment, the lens 38 is switched between the state in which the lens 38 is placed on the optical axis between the mirror 32 and the cone 40, and the state in which the lens 38 is not placed on the optical axis between the mirror 32 and the cone 40. When the lens 38 is placed on the optical axis between the mirror 32 and the cone 40, as shown in FIG. 6, the measurement light is radiated to the eye to be examined 100 so that the measurement light is incident to the eye parallel to the optical axis while the incident position of the measurement light is changed by the interference optical system. Thus, the incident angle of the measurement light on the eye to be examined 100 becomes substantially constant, and even if the incident position of the radiated measurement light is shifted from the position of the apex of the cornea 102, the intensity of light reflected from the eye to be examined 100 is not reduced, and the intensity of the interfering light detected by the light detector 14 can be made sufficiently great.

The alignment mechanism 34 includes: an alignment optical system (not shown) for detecting the position of the measurement unit 60 relative to the eye to be examined 100; a cornea apex detection device (not shown) for detecting the position of the apex of the cornea 102 of the eye to be examined 100; and a position adjusting mechanism (not shown) for adjusting the position of the measurement unit 60 based on a result of the detections. As the alignment mechanism 34, an alignment mechanism used in a known ophthalmological device can be used, and therefore the detailed description thereof will be omitted.

Figure 2:
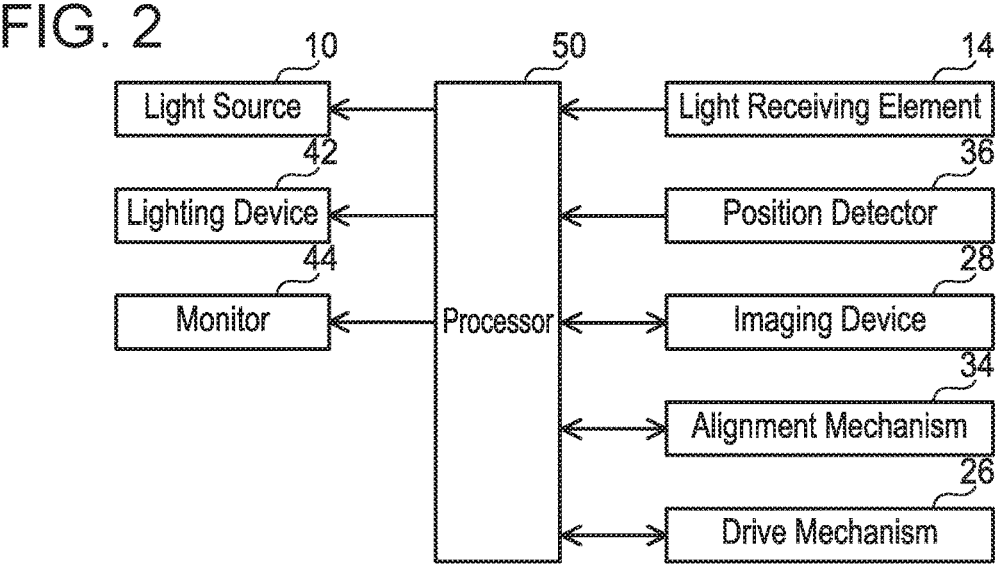
FIG. 2 is a block diagram of a control system of the ophthalmological device according to the present embodiment.

Next, the configuration of a control system of the ophthalmological device in the present embodiment will be described. As shown in FIG. 2, the ophthalmological device is controlled by the processor 50. The processor 50 includes a microcomputer (microprocessor) composed of a CPU, a ROM, a RAM. The light source 10, the lighting device 42, the monitor 44, the light detector 14, the position detector 36, the imaging device 28, the alignment mechanism 34, and the drive mechanism 26 are connected to the processor 50. The processor 50 controls ON/OFF of the light source 10 and the lighting device 42, controls the alignment mechanism 34 and the drive mechanism 26 to perform positional adjustment of the measurement unit 60, and controls the imaging device 28 to take an anterior eye image (reflected images of ring light) of the eye to be examined 100. The light detector 14 is connected to the processor 50, and an interfering signal corresponding to the intensity of the interfering light detected by the light detector 14 is inputted to the processor 50. The processor 50 performs Fourier transform on the interfering signal from the light detector 14, thereby specifying the positions of the anterior and posterior surfaces of the cornea 102 of the eye to be examined 100 and calculating the thickness of the cornea 102.

Figure 3:
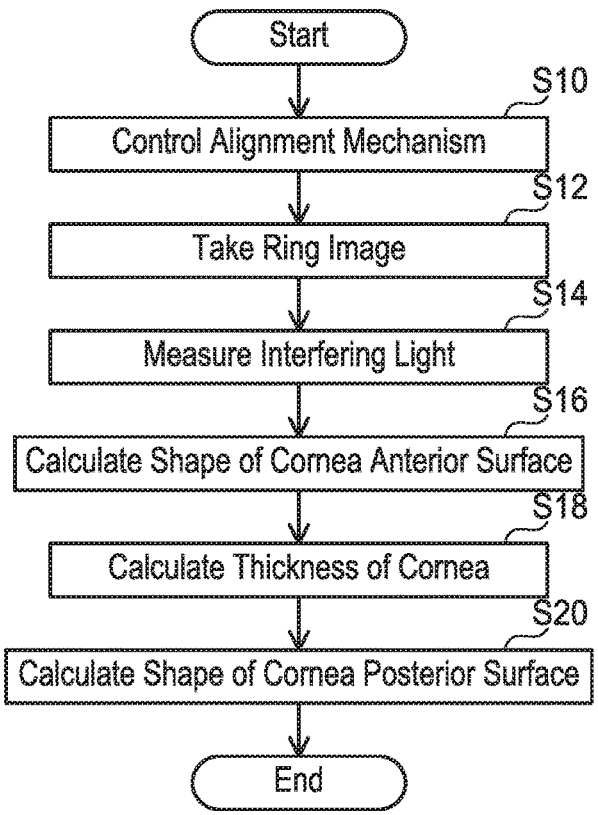
FIG. 3 is a flowchart showing an example of procedure of processing in the ophthalmological device according to the present embodiment.

Next, a procedure for measuring the shape of the anterior surface of the cornea 102 and the shape of the posterior surface of the cornea 102 of the eye to be examined 100 using the ophthalmological device of the present embodiment will be described. When an examiner operates a switch (a switch for inputting start of measurement) which is not shown, as shown in FIG. 3, the processor 50 controls the alignment mechanism 34 to perform positional adjustment of the measurement unit 60 relative to the eye to be examined 100 (step S10). That is, by the alignment mechanism 34, the processor 50 detects the position of the apex of the cornea 102 of the eye to be examined 100 and positions the apex of the cornea 102 on the optical axis of the measurement unit 60. Thus, the position in the xy direction (vertical-transverse direction) and the position in the z direction (forward-backward direction) of the measurement unit 60 relative to the eye to be examined 100 are adjusted. When the measurement unit 60 is positioned, the apex of the cornea 102 is positioned at the center of the anterior eye image taken by the imaging device 28. In addition, the processor 50 drives the drive mechanism 26 to adjust the beam expander 21. Thus, the position of the focal point of light radiated from the light source 10 to the eye to be examined 100 coincides with a predetermined position (e.g., the anterior surface of the cornea 102) of the eye to be examined 100. In step S10, the convex lens 22 of the beam expander 21 is driven only in the optical-axis direction.

Next, the processor 50 turns on the lighting device 42 to radiate a plurality of ring light to the front surface of the cornea 102 of the eye to be examined 100, and takes reflected images of the plurality of ring light reflected from the eye to be examined 100 by the imaging device 28 (step S12). Since the measurement unit 60 is positioned relative to the eye to be examined 100 in step S10, as shown in FIG. 4, the ring light L1 to L6 radiated to the eye to be examined 100 are concentrically arranged about the apex of the cornea 102. The anterior eye image of the eye to be examined 100 and the reflected images of the ring light L1 to L6, taken by the imaging device 28, are stored in a memory of the processor 50 and displayed on the monitor 44. After the reflected images of the plurality of ring light L1 to L6 are taken, the processor 50 turns off the lighting device 42.

Next, the processor 50 turns on the light source 10, and causes the light detector 14 to measure interfering light (S14). That is, the processor 50 places the lens 38 on the optical axis, turns on the light source 10 to radiate measurement light to the eye to be examined 100, and detects interfering light composed of reflected light reflected from the eye to be examined 100 and the reference light by the light detector 14. An interfering signal outputted from the light detector 14 is stored in the memory of the processor 50. Here, in the detection of the interfering light by the light detector 14, the drive mechanism 26 is driven to scan the measurement light radiated to the eye to be examined 100 so that the measurement light is radiated to the same positions as the positions at which the ring light Li to L6 are radiated (see FIG. 4). That is, the measurement light radiated to the eye to be examined 100 is scanned in a ring shape around the apex of the cornea 102. The processor 50 stores, in the memory, the interfering signals for the plurality of incident positions P (incident positions P in FIG. 4) set in advance on the eye to be examined 100. The interfering signals stored in the memory are processed in step S18 described later. In scanning of the measurement light radiated to the eye to be examined 100 by the drive mechanism 26, the position at which the measurement light is radiated is detected by the position detector 36. As a result, the interfering signal for each incident position P can be properly obtained, whereby the measurement in step S14 can be accurately performed. In the measurement in step S14, since the lens 38 is placed on the optical axis, parallel light is radiated to the eye to be examined 100. As a result, the intensity of the interfering light detected by the light detector 14 can be increased.

Next, the processor 50 calculates the shape of the front surface of the cornea 102 of the eye to be examined 100 from the reflected images of the plurality of ring light L1 to L6 taken in step S12 (S14). A known method (for example, a method disclosed in Japanese Patent Application Publication No. 2011-167359, etc.) can be used for calculating the shape of the cornea surface from the reflected images of the ring light L1 to L6. For example, the processor 50 detects a white-black edge (boundary) of each reflected image of the ring light L1 to L6, and calculates the position of the ring image and an edge distance from the cornea center to the edge. Next, under the assumption that the ring image has an arc shape passing through the cornea apex, the cornea curvature at the position of the ring is calculated based on the calculated edge distance. The shape (radius of curvature, etc.) of the anterior surface of the cornea 102 calculated in step S14 is outputted to the monitor 44.

Next, the processor 50 processes the interfering signals for the plurality of incident positions P obtained in step S14 to calculate the cornea thicknesses at the plurality of incident positions P (S18). That is, the processor 50 Fourier analyzes on each interfering signal obtained by radiating the measurement light to the plurality of incident positions P, thereby specifying the position of the anterior surface and the position of the posterior surface of the cornea 102 of the eye to be examined 100 at each of the plurality of incident positions P. From the position of the anterior surface of the cornea 102 and the position of the posterior surface of the cornea 102, the thickness of the cornea 102 at the corresponding incident position P is calculated. In step S18, the thicknesses of the cornea 102 at all the incident positions P are calculated.

Figure 5:
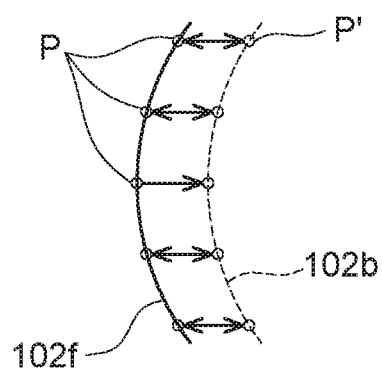
FIG. 5 is a diagram for explaining the procedure for calculating the shape of a cornea posterior surface from the shape of a cornea anterior surface and cornea thicknesses at the incident positions.

Next, the processor 50 calculates the shape of the posterior surface of the cornea 102 from the shape of the anterior surface of the cornea 102 obtained in step S16 and the thicknesses of the cornea 102 at the incident positions P obtained in step S18 (S20). As shown in FIG. 5, a position P' on the posterior surface 102*b* of the cornea 102 corresponding to each incident position P can be specified from the shape of the cornea anterior surface 102*f* obtained in step S16 and the thickness of the cornea 102 at the incident position P. Thus, the positions P' on the posterior surface 102*b* of the cornea 102 corresponding to the respective incident positions P are specified. The processor 50 estimates the shape of the posterior surface 102*b* of the cornea 102 using the positions P' on the posterior surface 102*b* of the cornea 102 corresponding to the respective incident positions P. Various known mathematical methods can be used for estimating the shape of a curved surface when the coordinates of a plurality of points on the curved surface are given. The shape (radius of curvature, etc.) of the posterior surface 102b of the cornea 102 thus obtained is outputted to the monitor 44.

As is obvious from the above description, in the ophthalmological device according to the present embodiment, the shape of the posterior surface 102b of the cornea 102 is calculated from the shape of the anterior surface 102f of the cornea 102 obtained from the reflected images of the ring light L1 to L6 and the thicknesses of the cornea 102 at the incident positions P obtained from the interfering light. Thus, the shape of the cornea posterior surface 102b can be accurately measured.

While the embodiments of the present invention have been described in detail, these embodiments are for illustrative purposes only and are not intended to limit the scope of the claims. The techniques described in the claims include various modifications and changes made to the specific embodiments illustrated above.

For example, in the above embodiment, the incident position P of the measurement light radiated to the eye to be examined 100 is changed by driving the convex lens 24 of the beam expander 21 in the xy direction. However, a mechanism for changing the incident position of light radiated to the eye to be examined 100 is not limited thereto. For example, the incident position of light radiated to the eye to be examined 100 may be changed using a galvanometer mirror. In the above embodiment, the lens 38 is switched between the state in which the lens 38 is placed on the optical axis between the mirror 32 and the cone 40, and the state in which the lens 38 is not placed on the optical axis between the mirror 32 and the cone 40. Alternatively, the lens 38 may be always placed on the optical axis instead of such a configuration.

In the above embodiment, an example in which the interferometer of a Fourier domain type is used has been described. However, an interferometer of a time domain type may be used.

The technical elements explained in the present specification or drawings provide technical utility either independently or through various combinations. The present invention is not limited to the combinations described at the time the claims are filed. Further, the purpose of the examples shown by the present specification or drawings is to satisfy multiple objectives simultaneously, and satisfying any one of those objectives gives technical utility to the present invention.

What is claimed is:

1. An ophthalmological device comprising:
a ring image photographic optical system configured to radiate a plurality of concentric ring light to a cornea surface of an eye to be examined and take reflected images of the plurality of ring light reflected from the cornea surface of the eye;
an interference optical system configured to radiate measurement light to the eye, and detect interfering light composed of reflected light of the measurement light reflected from the eye and predetermined reference light, the interference optical system being further configured to change an incident position of the measurement light radiated to the eye; and
a processor configured to calculate a posterior surface shape of the cornea of the eye based on an anterior surface shape of the cornea of the eye and thicknesses of the cornea at a plurality of the incident positions, wherein the anterior surface shape of the cornea of the eye is determined based on the reflected images of the plurality of ring light obtained in the ring image photographic optical system, and the thicknesses of the cornea at the incident positions are determined based on the interfering light at the incident positions obtained in the interference optical system.

2. The ophthalmological device according to claim 1, wherein:
each of the incident positions is on a circumference of a preset circle which is preset so as to encircle a cornea apex of the eye,
the interference optical system is configured to radiate the measurement light at each of the incident positions, and
the processor is configured to determine the thicknesses of the cornea of the eye at the incident positions.

3. The ophthalmological device according to claim 2, wherein the interference optical system comprises an optical member configured to radiate the measurement light such that the measurement light enters the eye parallel to an optical axis of the eye while the incidence position of the measurement light is changed by the interference optical system.

4. The ophthalmological device according to claim 3, further comprising an incident position sensor configured to detect the incident position of the measurement light that is changed by the interference optical system.

5. The ophthalmological device according to claim 1, wherein the interference optical system comprises an optical member configured to radiate the measurement light such that the measurement light enters the eye parallel to an optical axis of the eye while the incidence position of the measurement light is changed by the interference optical system.

6. The ophthalmological device according to claim 1, further comprising an incident position sensor configured to detect the incident position of the measurement light that is changed by the interference optical system.

* * * * *